Feb. 4, 1964 C. FISCHER Plant Pat. 2,353
GLADIOLUS PLANT
Filed Sept. 18, 1962
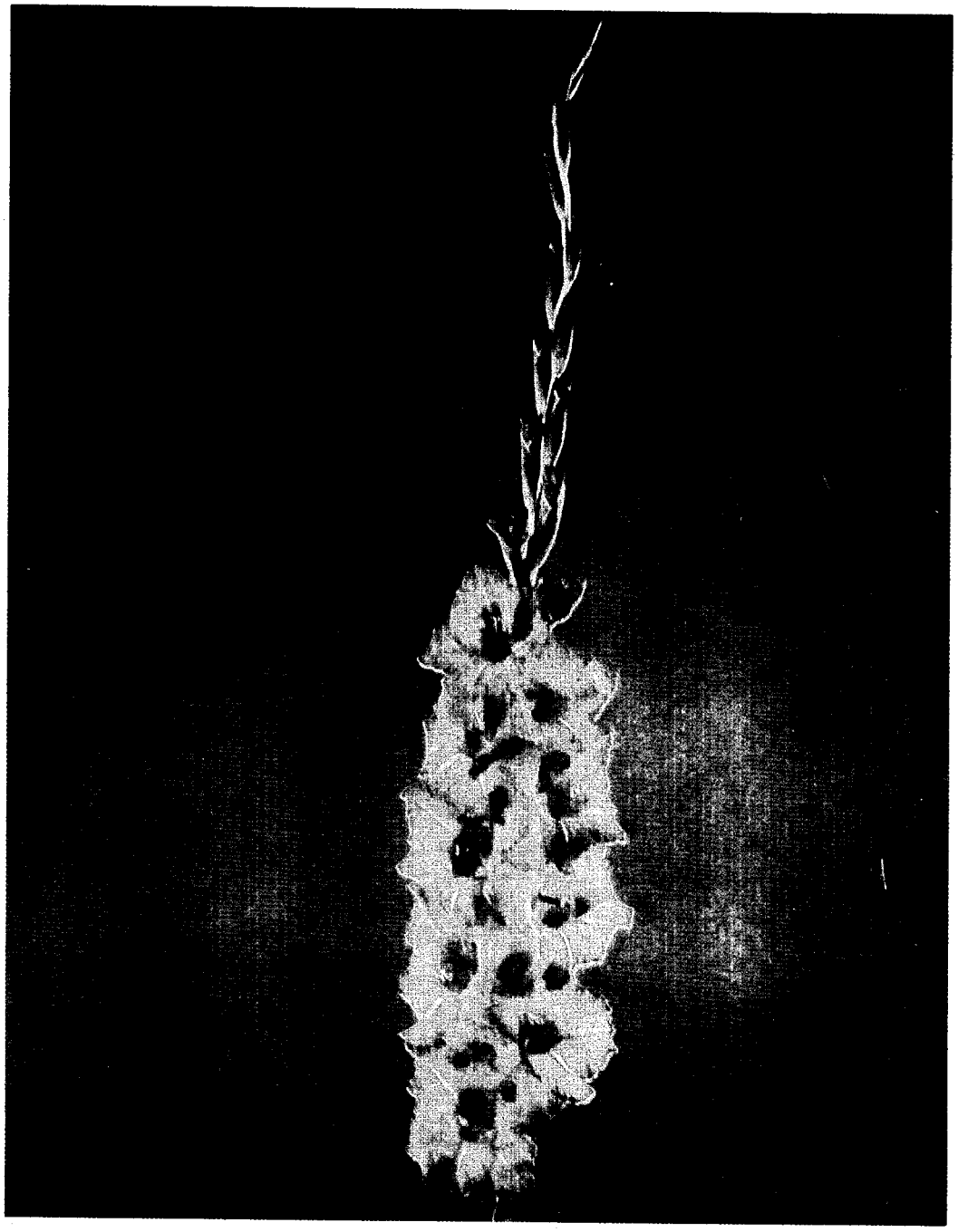
Inventor
Carl Fischer
By: Robb & Robb
Attorneys.

United States Patent Office

Plant Pat. 2,353
Patented Feb. 4, 1964

2,353
GLADIOLUS PLANT

Carl Fischer, St. Charles, Minn., assignor to Imperial Flowers Limited, Leamington, Ontario, Canada, a corporation of Canada Filed Sept. 18, 1962, Ser. No. 224,582
1 Claim. (Cl. Plt.—85)

The present invention relates to a new and distinct variety of gladiolus plant which was originated by me by crossing the variety known as "Maytime" (Plant Patent No. 1,591) with an unnamed and unpatented seedling derived from a cross of "Gloaming" (unpatented) and "Rose O'Day" (unpatented), the variety "Maytime" being the seed parent and the unnamed seedling being the pollen parent.

The primary objective of this breeding was to produce a new gladiolus variety having extremely good vigor and the ability to grow under almost any circumstances. This objective was fully achieved, along with other desirable improvements, as evidenced by the following unique combination of characteristics which are outstanding in the new variety and which distinguish it from its parents, as well as from all other varieties of which I am aware:

(1) An extremely robust habit of growth;

(2) Unusually good resistance to Fusarium yellow, Sclerotina dry rot and Septoria leaf spot;

(3) Unusually good temperature tolerances covering a wide range between hot and cold weather; and (4) A distinctive and attractive Currant Red general color tonality of the flowers which shade deepest at the tip of the petals and on the reverse thereof, with the lip petals of the individual florets having sharp white lines.

My new variety resembles the variety known as "Modern Times" (unpatented) more than any other, but differs principally therefrom by being more rugged, taller and healthier in its habits of growth; an ability to withstand more heat and cold; larger florets; and a heavier substance of the flower petals.

Asexual reproduction of my new variety by cormels through several generations, as performed by me at St. Charles, Minnesota, shows that the foregoing characteristics and distinctions come true to form and are established and transmitted through succeeding propagations.

The accompanying drawing shows a typical specimen flower spike of my new variety, with the flowers in different stages of development ranging from closed buds through partially open buds to fully open flowers, as depicted in color as nearly true as it is reasonably possible to make the same in a color illustration of this character.

The following is a detailed description of my new variety, with color terminology in accordance with the Horticultural Colour Charts issued by the British Colour Council and the Royal Horticultural Society, except where general color terms of ordinary dictionary significance are obvious:

Locality where grown and observed: St. Charles, Minnesota.

Propagation: Holds its distinguishing characteristics through succeeding propagations by plantings derived from cormels.

*Plant*

Growth: Extremely rugged; prolific propagator; ranges from 62 inches to 64 inches tall.

Blooming habit: Mid-season bloomer in the Northern latitudes of the United States; comes into bloom from large bulbs in about 85 days.

Stems: Straight; willowy.

*Diameter at base.*—About ⅜ inch.

*Color.*—Rose purple just above the bulb, as well as purplish in color at flowerhead and bud sheaths.

Foliage: Droopy; relatively narrow (about 1½ inches wide); leaves measure about 30 inches tall to the arch thereof when drooping, but usually range between 40 inches and 48 inches in overall length. Color—healthy green.

Disease resistance: Unusually good resistance to Fusarium yellows, Sclerotina dry rot and Septoria leaf spot, as determined by comparison with other varieties grown in my fields near St. Charles, Minnesota, in irrigated black loam soil.

Corms (bulbs): Long-lived; husks cover corms well and have a deep rose cast. Color of flesh—from Brick Red, Plate 016/1 to Brick Red, Plate 016/2.

*Flower*

Spike: Tall; willowy; flowerhead ranges from about 26 inches to 28 inches long; average spike bears from 18 to 20 buds, with 7 or 8 florets open at once, and with 5 or 6 buds showing color.

Bud:

*Size.*—About 2½ inches long when opening.

*Opening.*—5 or 6 buds show color at one time; poor opener when cut with tight buds.

Flower:

*Arrangement.*—Florets are formally placed in a double row on the stem and almost always face forward.

*Size.*—Lower florets measure from 4 inches to 4½ inches in diameter, with upper florets being progressively smaller.

*Form.*—Florets are round, recurved and slightly ruffled.

*Keeping qualities.*—Average keeper when cut with open flowers.

Petals:

*Shape.*—Round; recurved.

*Size.*—Outer petals—about 2¼ inches wide. Lip petal—about 1½ inches wide.

*Aspect.*—Average substance; smooth surface.

*Fragrance.*—None.

*Color.*—General color effect is Currant Red, Plate 821, with deepest color at the tip of the flower petals and on the reverse surfaces of the florets; upper petals shade to Blood Red, Plate 820/3, while lip petals have sharp white lines, with calyx being Currant Red, Plate 821.

*Reproductive Organs*

Stamens: Color—purple.

Pistil: Color—tinted Currant Red.

I claim:

A new and distinct variety of gladiolus plant, substantially as herein shown and described, characterized particularly as to novelty by an extremely robust habit of growth, good disease resistance, good temperature tolerances over a wide range of heat and cold, and a distinctive and attractive generol color tonality of the flowers corresponding to Currant Red, with deepest color at tip of petals and on reverse surfaces of florets, the upper petals of the florets shading to Blood Red, and the lip petals having sharp white lines.

No references cited.